United States Patent [19]

Kronheim et al.

[11] Patent Number: 5,484,887
[45] Date of Patent: Jan. 16, 1996

[54] HOMOGENEOUS INTERLEUKIN 1

[75] Inventors: Shirley R. Kronheim; Carl J. March; Paul J. Conlon, III; Thomas P. Hopp, all of Seattle, Wash.

[73] Assignee: Immunex Corporation, Seattle, Wash.

[21] Appl. No.: 676,533

[22] Filed: Nov. 30, 1984

Related U.S. Application Data

[63] Continuation-in-part of Ser. No. 635,006, Jul. 27, 1984, abandoned, which is a continuation-in-part of Ser. No. 622,201, Jun. 19, 1984, abandoned.

[51] Int. Cl.$^6$ .............................. C07K 14/545; C07K 1/00
[52] U.S. Cl. .................... 530/351; 424/85.2; 930/141; 530/412; 530/413; 530/414; 530/417; 530/351; 435/69.52
[58] Field of Search ..................... 530/351, 412, 530/413, 414, 417

[56] References Cited

U.S. PATENT DOCUMENTS

| | | | |
|---|---|---|---|
| 4,172,091 | 10/1979 | De Maeyer et al. | 424/85 |
| 4,406,830 | 9/1983 | Fabricius et al. | 530/351 |
| 4,508,833 | 4/1985 | Sonneborn et al. | 530/351 |
| 4,546,161 | 10/1985 | Harvey et al. | 530/413 |
| 4,762,914 | 8/1988 | Auron et al. | 530/351 |
| 4,766,069 | 8/1988 | Auron et al. | 435/240.1 |
| 4,770,781 | 9/1988 | Schmidt et al. | 530/351 |
| 4,774,320 | 9/1988 | Tagliabue et al. | 530/351 |

FOREIGN PATENT DOCUMENTS 0092163  10/1983  European Pat. Off..

OTHER PUBLICATIONS

Sofer et al. *BioTechniques* Nov./Dec. 1983 pp. 198–203.
Dean et al. *J. Chromatography* 165, 1979, pp. 301–319.
Auron et al. *PNAS* 81, 1984, pp. 7907–7911.
Windle et al. *J. Immunol* 132, 1984, pp. 1317–1322.
Mizel, "Interleukin 1 and T Cell Activation", *Immunol. Rev* vol. 63, 1982, pp. 51–72.
*Dye–Ligand Chromatography*, Amicon Corporation (Lexington, Mass.) (1980) (Chapters 1–3).
March et al., "Cloning, sequence and expression of two distinct human interleukin–1 complementary DNAs," *Nature* 315:641–647 (1985).
G. Blyden et al., "Purification and Properties of Human Lymphocyte Activating Factor (LAF)," 118 *J. Immunol.* 1631–1638 (1977).
L. B. Lachman et al., "Partial Purification of Human Lymphocyte–Activating Factor (LAF) By Ultrafiltration and Electrophoretic Techniques," 119 *J. Immunol.* 2019–2023 (1977).
A. Togawa et al., "Characterization of Lymphocyte–Activating Factor (LAF) Produced By Human Mononuclear Cells: Biochemical Relationship of High and Low Molecular Weight Forms of LAF," 122 *J. Immunol.* 2112–2118 (1979).
S. B. Mizel et al., "Characterization of Lymphocyte–Activating Factor (LAF) Produced by a Macrophage Cell Line, P388D$_1$, II. Biochemical Characterization of LAF Induced by Activated T Cells and LPS," 120 *J. Immunol.* 1504–1508 (1978).
S. B. Mizel et al., "Physicochemical Characterization of Lymphocyte–Activating Factor (LAF)," 122 *J. Immunol.* 2167–2172 (1979).
S. B. Mizel et al., "Purification to Apparent Homogeneity of Murine Interleukin 1," 126 *J. Immunol.* 834–837 (1981).
P. T. Lomedico et al., "Cloning and expression of murine interleukin–1 cDNA in *Escherichia coli*," 312 *Nature* 458–462 (1984).
G. Di Sabato, "Purification and initial characterization of rat interleukin2," 79 *Proc. Natl. Acad. Sci USA* 3020–3023 (1982).
"Minisymposium on Regulation of Connective Tissue Cells by Immune and Inflammatory Cells," *Lymphokine Res.* 1(2):53 (1982).
K. Welte et al., "Purification of Human Interleukin 2 to Apparent Homogeneity and its Molecular Heterogeneity," 156 *J. Exp. Med.*, 454–464 (1982).
O. Acuto, "An Efficient Method for Purification of Human T–Cell Growth Factor," 53 *J. Immunol. Methods* 15–26 (1982).
J. J. Oppenheim et al., "Interleukin 1 is more than an interleukin," *T Lymphocytes Today* 89–95 (1983).
L. B. Lachman, "Human interleukin 1: purification and properties," 42 *Federation Proceedings* 2639–2645 (1983).
A. Kock et al., "Purification of Human Interleukin 1 by High–Performance Liquid Chromatography," 296 *J. Chromat.* 293–300 (1984).
Matsushima et al, *Lymphakine Res.* Oct. 1984 p. 259 (abstract only).
C. A. Dinarello et al., PNAS 74:4624, 1977.
K. Welte et al., J. Exp. Med. 156:454, 1982.
Mosley, et al. *Proc. Nat'l Acad. Sci. (USA)* 84: 4572, 4576 (1987).

*Primary Examiner*—Garnette D. Draper
*Assistant Examiner*—Lorraine M. Spector
*Attorney, Agent, or Firm*—Foley & Lardner

[57] ABSTRACT

Interleukin 1 has been purified by use of various techniques including ion exchange chromatography and dye-ligand affinity chromatography. By these techniques, interleukin 1 has been purified to homogeneity. The high purification of interleukin 1 has enabled the amino acid composition of this protein to be ascertained and its amino acid sequence to be partially determined.

12 Claims, 1 Drawing Sheet

HOMOGENEOUS INTERLEUKIN 1

CROSS REFERENCE TO RELATED APPLICATION

This is a continuation-in-part of U.S. patent application Ser. No. 635,006, filed Jul. 27, 1984, which in turn is a continuation-in-part of U.S. patent application Ser. No. 622,201, filed Jun. 19, 1984 both abandoned.

TECHNICAL FIELD

The present invention relates to interleukin 1 (hereinafter "IL-1"), and more particularly to purified IL-1 and a process for producing same.

BACKGROUND OF THE INVENTION

IL-1, formally known in the literature as "lymphocyte activating factor" or "LAF," is a hormone secreted by macrophages while undergoing an immune response. This protein factor regulates a wide range of immunological and non-immunological responses. For instance, it is considered that IL-1 mediates activities referred to as endogenous or leukocytic pyrogen, B-cell activating factor (BAF), epidermal cell thymocyte activating factor (ETAF), leukocyte endogenous mediator (LEM), bone resorption factor active in rheumatoid arthritis, and a variety of other activities. As such, IL-1 shows promise for therapeutic mediation of immune response, which is defined herein to include the aforementioned activities.

Although researchers have identified many of the biological properties of IL-1, the chemical nature of this hormone is not well understood. To date, this has been hampered, at least in part, by the unavailability of sufficient quantities of IL-1 in purified form to carry out necessary investigations.

Attempts have been made in the past to purify and characterize IL-1 derived from both human and murine sources. For instance, Mizel, 122 *J. Immunol.* 2167–2172 (1979), reported the production of murine IL-1 from the macrophage cell line, $P388D_1$, cultured in a supplemented growth medium together with phorbol myristic acetate as an activating agent. The IL-1 from the culture fluid was subjected to ammonium sulfate precipitation, diethyl amino ethyl ("DEAE") cellulose column chromatography, ultrafiltration and Sephacryl S200 column chromatography. The resulting active fractions were analyzed by sodium dodecyl sulfate ("SDS")-polyacrylamide gel electrophoresis (PAGE) and were found to have a molecular weight in the range of 12,000 to 16,000 daltons. Through isoelectrofocusing ("IEF") in polyacrylamide gels, the pI of the IL-1 was found to be in tile range of from 5.0 to 5.4.

In a subsequent communication Mizel et al., 126 *J. Immunol.* 834–837 (1981), discussed purifying IL-1 from the same $P388D_1$ cell line as used in Mizel, supra, to "apparent homogeneity" by ammonium sulfate precipitation, phenyl Sepharose chromatography, Ultrogel AcA54 gel filtration chromatography and preparative flat-bed IEF. From the IEF, the pI of the IL-1 was measured to be about 4.9 to 5.1. Through gel electrophoresis the molecular weight of the IL-1 molecule was determined to be approximately 14,000 daltons.

Researchers have also investigated IL-1 produced from human peripheral blood leukocytes and monocytes. Blyden et al., 118 *J. Immunol.* 1631–1638 (1977), disclosed a protocol for concentrating IL-1 prepared from human peripheral blood leukocytes by Sephadex G-100 column chromatography. This procedure was reported to result in a four-to-five fold concentration of the crude IL-1. DEAE-Bio-Gel A anion exchange chromatography was employed to remove the albumin from the serum used during the preparation of the crude IL-1. Next, the collected active fractions were adsorbed onto a hydroxyapatite column. Fractions containing peak IL-1 activity were then applied to a CM-Bio-Gel A cationic exchange resin. By these procedures, about 20% of the initial IL-1 was recovered. The resulting IL-1 was found to have a molecular weight of about 13,000 daltons and a pI of approximately 6.8 to 7.2.

Crude IL-1 prepared from human leukocytes by Togawa et al., 122 *J. Immunol.* 2112–2118 (1979) was initially processed by membrane filtration and then applied to a Bio-Gel P-100 chromatography column which disclosed two major peaks of activity, one in the range of from 12,000 to 22,000 daltons and another in the range of about 50,000 to 70,000 daltons. Active fractions in the lower molecular weight region of the Bio-Gel P-100 column were pooled, applied to a Blue Sepharose column, and then applied to a DEAE-cellulose ion-exchange chromatography column. Thereafter, the IL-1 containing fractions were pooled and applied to a hydroxyapatite chromatography column. Togawa et al. discovered that when the lower molecular weight IL-1 activity resulting from each of these procedures was reconstituted with 2% human serum, concentrated and rechromatographed on Bio-Gel P-100, a significant portion of the higher molecular weight activity appeared.

In a more recent study, Lachman, 42 *Federation Proceedings* 2639–2645 (1983), reported preparing IL-1 by culturing peripheral blood monocytes or leukemic cells obtained from acute monocytic leukemia or acute myelomonocytic leukemia patients in a serum supplemented culture medium together with lipopolysaccharide ("LPS") to stimulate IL-1 production. Hollow fiber diafiltration and ultrafiltration were used to separate a lower molecular weight activity from most of the serum proteins. This lower weight activity was subjected to isoelectrofocusing in an Ampholine and sucrose gradient. From this procedure, the IL-1 activity was found to have a pI of about 6.8 to 7.2. The isoelectrofocused IL-1 activity was then subjected to SDS-PAGE which indicated that the human IL-1 being analyzed had a molecular weight of about 11,000 daltons. Lachman reported that the overall recovery of IL-1 activity from the above procedures was poor, in the range of about 4%.

SUMMARY OF THE INVENTION

The present invention relates to IL-1, the purification of human IL-1 to homogeneity and the determination of the amino acid composition and partial amino acid sequence of the homogeneous IL-1. In accordance with the present invention, crude preparations of IL-1 are purified by a combination of ion-exchange chromatography and affinity chromatography procedures. The affinity chromatography portion of the purification process employs a dye-ligand coupled to an insoluble matrix. Based on the prior art, it is contemplated that the same purification process may be successfully employed for IL-1 from other mammalian species, such as murine, bovine or porcine IL-1.

Once purified to homogeneity, the amino acid composition and sequence of the IL-1 molecule is analyzed. The amino acid composition of the molecule is ascertained by use of an amino acid analyzer. The amino acid sequence of the IL-1 molecule is determined by direct Edman degradation technique and also by initially fractionating the molecule, separating the fragments by high pressure liquid chromatography ("HPLC") and then analyzing the HPLC fractions that are found to contain IL-1 peptides by the Edman degradation method.

BRIEF DESCRIPTION OF THE DRAWINGS

The details of a typical embodiment of the present invention will be described in connection with the accompanying drawings in which.

DESCRIPTION OF THE INVENTION

Preparation of IL-1

Crude preparations are prepared from peripheral blood leukocytes. The leukocytes are separated from whole blood by well known techniques, such as by centrifugation over a volume of Ficoll/Hypaque solution. The leukocytes removed from the blood are cultured in vitro in a culture medium containing an appropriate stimulating agent to induce IL-1 secretion. After an optimum culture period, the supernatant is harvested by centrifugation and stored until used.

Rather than being obtained from leukocytes removed from whole blood, IL-1 can alternatively be prepared from monocytes derived from any monocyte rich source. Such monocyte sources include monocytic leukemic spleen cells, lymph cells and alveolar macrophages.

The medium used to culture the peripheral blood leukocytes may consist of commercially available media, such as Eagle's Minimum Essential Medium ("MEM") or Roswell Park Memorial Institute ("RPMI") medium. Additives, which may be individually or in combination added to the culture medium, include glutamine, HEPES buffer and various antibiotics, such as gentamycin, penicillin and streptomycin. In the past, serum also has been commonly used as an additive. However, applicants have discovered that in the procedures of the present invention, purification of IL-1 from the culture supernatant is facilitated if serum is not used in the culture. Although not employing serum has been found to result in a three-to-five fold reduction in the quantity of IL-1 produced in culture, the absence of serum also results in a 100-fold reduction in total protein produced, which lessens the complications involved in the purification of the IL-1.

Preferable stimulating agents used in conjunction with the present invention include *Staphylococcus aureus* or LPS extracted from *Escherichia coli*. In addition, phorbol esters, such as phorbal myristate 13-acetate, may be employed as a stimulating agent.

The process of culturing the leukocytes to induce secretion of IL-1 may be carried out in various environmental conditions. Preferably, however, the cultures are maintained in the temperature range of approximately 35°–38° C. in a humidified atmosphere of approximately 5–10% $CO_2$ in air. The quantity of IL-1 released by stimulation of peripheral blood leukocytes with an activating agent varies with time. Applicants have found that optimum levels of IL-1 expression are reached at approximately 24 hours after stimulation.

ASSAYS/ANALYSIS

A thymocyte proliferation assay and a protein assay are employed in conjunction with the present invention to monitor the IL-1 activity level and the protein content of the samples being purified. Also, SDS-PAGE and two-dimensional gel electrophoresis are used to analyze the IL-1 activity during the purification process.

Thymocyte Proliferation Assay

This assay involves ascertaining the capacity of a sample of IL-1 to induce proliferation of thymocytes derived from CD-1 mice. Briefly, approximately $1\times10^6$ thymocyte cells obtained from 10 to 12 week old CD-1 mice (Charles River Breeding Laboratories, Wilmington, Mass.) are seeded in round bottom microplate wells (Corning Plastics, Corning, N.Y.) in the presence of three-fold serial dilutions of IL-1 containing samples. The thymocyte cells are cultured in 150 ul of MEM containing 50 units/milliliter ("U/ml") penicillin, 50 micrograms/milliliter ("ug/ml") streptomycin, 2 millimolar ("mM") glutamine, 0.2 mM gentamycin, 10 mM HEPES buffer, ("Supplemented MEM"), pH 7.4, together with 3% v/v human serum and $10^{-5}$ M 2-mercaptoethanol. The samples are cultured for 72 hours at 37° C. in an atmosphere of 5% $CO_2$ in air. Thereafter the cultures are pulsed for approximately 4 hours with 0.5 microcuries ("uCi") of tritiated thymodine ("$^3$H-Tdr"), (New England Nuclear, Boston, Mass., 2 Ci/mM specific activity), after which the cultures are harvested onto glass fiber filter strips, for instance with the aid of a multiple-automated sample harvester. $^3$H-Tdr incorporation is then measured by liquid scintillation counting. Details of this procedure are disclosed in Gillis et al., 120 *J. Immunol.* 2027 (1978).

By this assay procedure, only the CD-1 thymocyte cells cultured in the presence of IL-1 incorporate $^3$H-Tdr in a dose dependent manner. CD-1 cells cultured in the absence of IL-1 incorporate only background levels of $^3$H-Tdr. IL-1 activity is calculated from the linear portion of the $^3$H-Tdr incorporation data in a manner similar to the procedure used by Gillis et al., supra, for determining interleukin-2 activity. Units of IL-1 activity are determined as the reciprocal dilution of a sample which generates 50% of maximal thymocyte $^3$H-Tdr incorporation as compared to a laboratory standard. For example, if a sample generates 50% of maximal thymocyte $^3$H-Tdr incorporation at a dilution of 1:15, then one unit ("U") of IL-1 is found in $\frac{1}{15}$ of the 150 microliter ("ul") assay volume, or 10 ul is said to contain one U of activity. The total sample would, therefore, contain 100 U [1,000 (ul/ml) 10 ul (per U)] of IL-1 activity/ml. See Gillis et al., supra.

Protein Assay

The protein content of the purification samples is determined by Biorad protein assay which is commercially available from Biorad, Richmond, Calif. This assay employs bovine serum albumin as a standard. The principles and details of this assay are discussed in Bradford, 72 *Anal. Biochem.* 248 (1976).

Gel Electrophoresis

The culture supernatant and chromatography column fractions are analyzed by SDS-PAGE to monitor the purification procedures of the present invention. This assay is conducted according to the gel stacking procedure of Laemmli, 227 *Nature (London)* 680 (1970). The assay employs 0.75 mm SDS slab gels using a 10–20% gradient of polyacrylamide gel. The gels are run at a constant 30 mA current. The resulting gel samples are silver stained, such as by the method described in Oakley et al., 105 *Anal. Biochem.* 361 (1980).

The particular assay samples that contain a high salt concentration are initially dialyzed against 0.001% SDS in 0.1 mM $NH_4HCO_3$ and then dried under a vacuum. The dried residue is dissolved in a reducing buffer (2% SDS), 1% 2-mercaptoethanol prior to the SDS-PAGE process.

Two-Dimensional Polyacrylamide Gel Electrophoresis

After completion of the purification procedures of the present invention, the IL-1 is analyzed by two-dimensional polacrylamide gel electrophoresis by the method described in Sammons et al., 2 *Electrophoresis* 135 (1981). In the procedure lyophilized IL-1 samples are resuspended in 20 ul of SDS solubilization buffer composed of 1% (w/v) cyclohexy-laminoethane, 2% (w/v) SDS, 2% 2-mercaptoethanol, 10% glycerol in water. The samples are heated to 100° C. for 10 minutes. After two hours of prefocusing, samples (solubilized for 10 min. in SDS at 100° C.) are applied to the first dimension gel and focused for 20 hours at a constant voltage of 600 volts. The first dimension focusing gels are scanned directly with a pH gradient gel scanner. Thereafter the gels are rinsed in equilibration buffer [9.3% (v/v) glycerol; 50% (v/v) Tris-SDS buffer (30 g Tris, 2 g. DSD per liter, adjusted to pH 6.8 with concentrated HC); 1% (w/v) SDS; 0.8% (v/v) 2-mercaptoethanol in water] for 2 minutes, placed on top of the second dimension gel and then covered with low temperature melting agarose. The second dimension electrophoresis (10–20% linear gradient of acrylamide) is conducted at a constant current of 40 mA/gel until the dye front reaches the bottom of the gel. After fixation in 50% (v/v) ethanol and 10% (v/v) glacial acetic acid, the gels are stained by color silver nitrate method of Sammons et al., supra.

Purification of IL-1

The supernatant resulting from the blood leukocyte culture as prepared by the above procedure is purified by cation exchange chromatography, anion exchange chromatography, and affinity chromatography employing a dye-ligand coupled to a column matrix. All chromatography fractions are assayed for IL-1 activity and protein concentration. Where appropriate, pH and conductivity are measured. Following each chromatography step, samples are analyzed by SDS-PAGE. In addition, after completion of the affinity chromatography procedure, active fractions are analyzed by two-dimensional polyacrylamide gel electrophoresis as discussed above.

A suitable column for the cation exchange chromatography process is composed of sulfopropyl Sephadex C-25 (Pharmacia Fine Chemicals, Piscataway, N.J.). Preferably, the column is equilibrated with buffer prior to application of the IL-1 sample and then washed with the same or different buffer after the IL-1 sample has been applied to the column to remove nonbound protein without elution of IL-1 activity. Elution of the IL-1 from the column is carried out with a buffered eluant of sufficient pH to disassociate the IL-1 from the column.

The pooled active fractions from the cation exchange chromatography procedure are further purified by anion exchange chromatography. Applicants have found that a suitable column material for this purpose is DEAE-Sephacel. The DEAE-Sephacel column is equilibrated with a buffer and the sample concentrate applied to the column. Elution is initially carried out with the starting buffer and then subsequently with a linear salt gradient in the same buffer. Fractions are collected and analyzed as discussed above.

Figure 1:
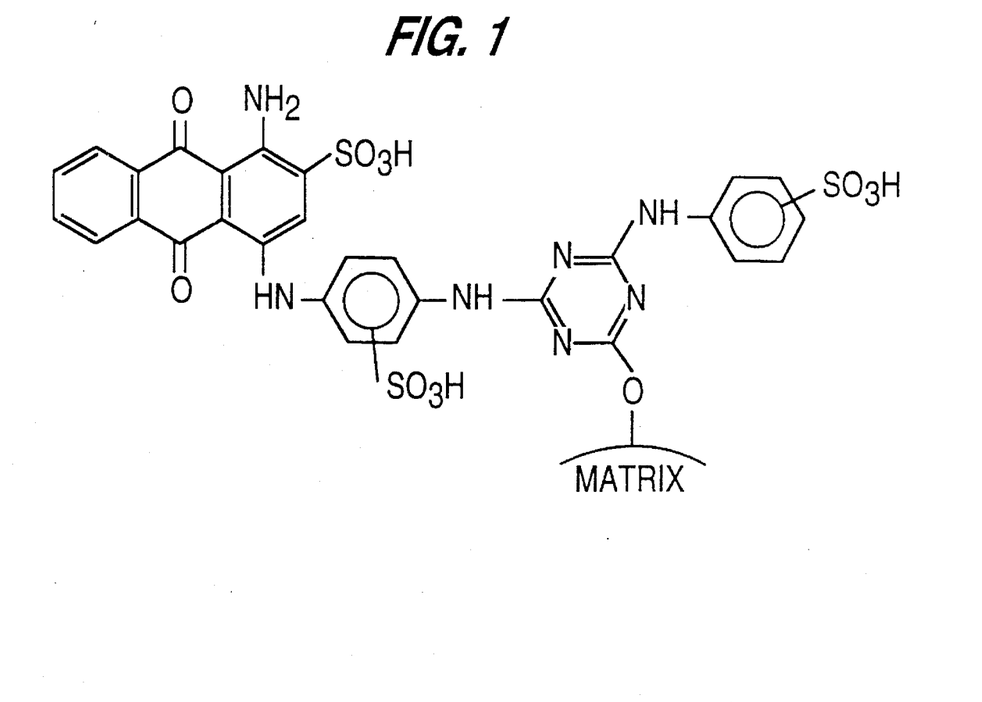
FIG. 1 illustrates a partial structural formula for blue dye-ligand.
Figure 2:
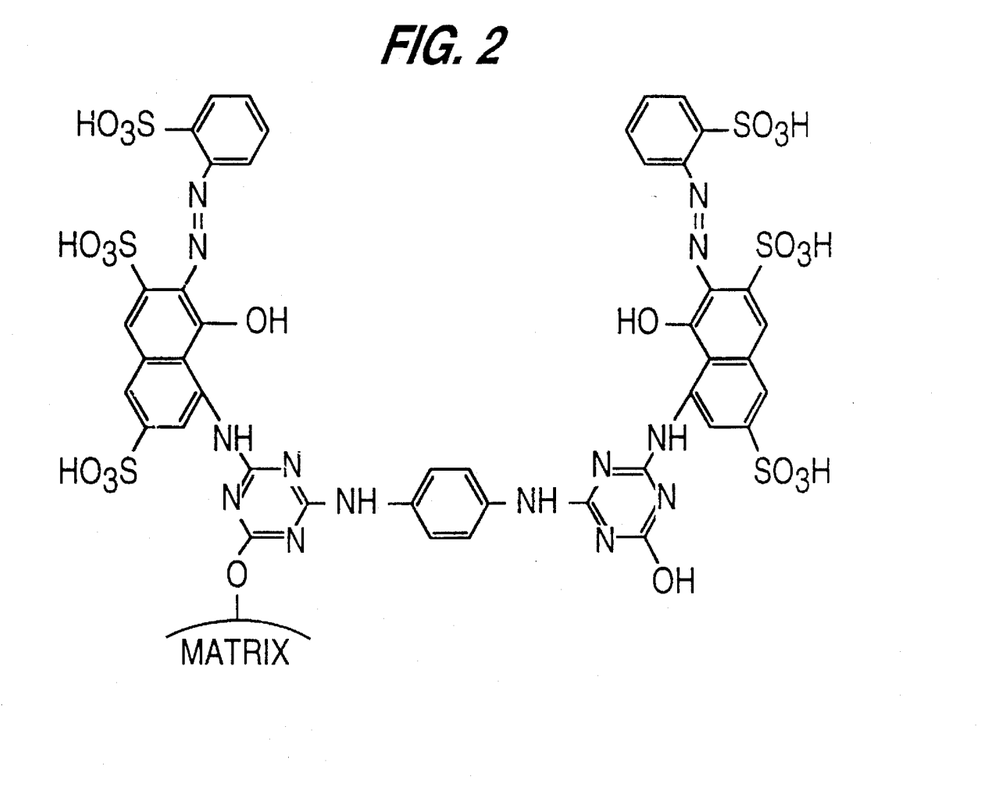
FIG. 2 illustrates a partial structural formula for red dye-ligand.

The IL-1 in the pooled active fractions from the DEAE-Sephacel column is further purified by affinity column chromatography employing a synthetic triazinyl textile dye-ligand coupled to a support matrix. Various dye colors may be employed including blue or red. The dye is coupled to an appropriate column matrix composed of, for instance, agarose, polyacrylamide, cellulose or silica-based inorganic materials via an ether linkage to the triazine ring or alternatively via a primary amine or an anthraquinone group of the dye. Rather than being bound directly to a support matrix, the dye can be bound to high molecular weight dextran with the dextran then immobilized to a column matrix. Partial chemical structures of blue and red dye-ligands coupled to a matrix are shown in FIGS. 1 and 2, respectively. It is to be understood that these dye structures can be modified to form analogs, for instance by exchanging the positions of the sulfonated anthraquinone group relative to the triazine ring or by substituting a sulfonate salt for the sulfonic acid substituents. See Fulton, *Dye-Ligand Chromatography*, Lexington, Mass.: Studio 6, Inc. (1980).

Prior to applying the IL-1 containing fractions purified over SP-Sephadex and DEAE-Sephacel to the dye-ligand column, it may be necessary to lower the ionic strength of the pooled active fractions. Also, the presence of a divalent cation, such as $Mg^{++}$ or $Ca^{++}$, may enhance the binding of IL-1 to the dye-ligand. The column is equilibrated with an appropriate buffer, such as Tris-HCL, and then the pooled DEAE fractions containing IL-1 activity are applied to the column. Thereafter, the column is washed with the same starting buffer and then elution is carried out with a linear salt gradient in the same buffer or a specific soluble ligand. Fractions are collected and analyzed as discussed above.

Applicants have discovered that red triazinyl textile dye, when used under the stated column conditions, is especially highly specific for binding IL-1. A commercial brand of this red dye corresponding to FIG. 2 is "Procion" red (reactive red 120) (Imperial Chemical Industries). Applicants have also discovered that blue triazinyl textile dye when used under the stated column conditions is also highly specific for binding IL-1, i.e. approximately 80% as specific as red triazinyl textile dye. A commercial brand of blue dye is Cibacron® Blue 36A (Ciba AG).

By the aforementioned purification process, applicants have purified human IL-1 protein to greater than 99% purity while maintaining a high yield of about 53% from the starting supernatant. By the above-described assay procedures, applicants have determined that human IL-1 is composed of a singular molecular weight specie of approximately 17,500 daltons molecular weight. This molecular weight is somewhat heavier than those previously reported for either human or murine IL-1. Moreover, contrary to reports of other observers, no other molecular weight species of IL-1 were found by applicants. See Lachman, supra; Togawa et al., supra; Mizel et al., supra; and Blyden et al., supra. Nevertheless, because of the high yields of IL-1 experienced by applicants by use of the present invention, it is unlikely that any significant amounts of other lower molecular weight IL-1 species were lost during the aforementioned purification process. The true molecular weight for homogeneous human IL-1 is therefore 17,500 daltons.

Amino Acid Composition Analysis

In addition to making possible the biological study of IL-1 free from contamination by other proteins, the ability to prepare homogeneous IL-1 has enabled applicants to determine the amino acid composition of the IL-1 molecule. This information may be employed to assist in the cloning of the IL-1 gene and the production of large quantities of pure IL-1 for clinical trims and ultimately for clinical use.

Samples of purified IL-1 from the affinity chromatography procedure are analyzed for amino acid composition with an automated analyzer using ninhydrin detection. Observed peaks are integrated with commercially available recording integrator. Through this technique, applicants have determined the amino acid composition of the IL-1 molecule as summarized in Table I in Example 4, below.

Since the amino acid residue cysteine (Cys) is unstable to hydrolysis, this residue is not detected by automated ninhydrin analysis. The presence of the Cys residue was detected by the amino acid sequencing analysis, discussed below. Also, automated ninhydrin analysis does not distinguish aspartic acid residues from asparagine residues nor does it distinguish glutamic acid residues from glutamine residues. However, from the amino acid sequencing analysis, discussed below, an asparagine residue and six glutamine residues were detected in a N-terminal portion of the IL-1 molecule (consisting of 42 amino acid residues). Thus, in Table I the aspartic acid and asparagine residues are listed together, as are the glutamic acid and glutamine residues.

Amino Acid Sequence Analysis

Applicants have also investigated the amino acid sequence of the IL-1 molecule. Applicants have discovered that in the purified IL-1 prepared by the procedures set forth above, the N-terminus of this molecule is blocked. As such, the molecule is not readily amenable to the chemical analysis technique employed in automated amino acid sequencing apparatuses, and thus the amino acid sequence of the entire molecule could not be determined by standard analysis procedures. As a result, applicants employed a combination of two techniques to analyze the sequence of the N-terminal portion of the protein molecule.

As a first technique applicants subjected a rather large sample of over 11 ug of IL-1, as purified to homogeneity by the aforediscussed methods, to amino terminal Edman degradation sequence analysis with an automated sequencing apparatus. By this technique the first 20 residues of the N-terminal portion of the IL-1 molecule was found to be composed of the following sequence:

Ala-Pro-Val-Arg-Ser-Leu-Asn-Cys-Thr-Leu-Arg-Asp-Ser-Gln-Gln-Lys-Ser-Leu-Val-Met.

The 8th residue was deduced to be Cys. In the eighth cycle of the automated sequencing procedure no other residue was obtained in high yield, which points to the conclusion that the eighth residue is composed of Cys (which is not affirmatively detected by Edman degradation), a glycosylated threonine residue or a glycosylated serine (Ser) residue. These later two possibilities were elmininated since, as discussed below, no glucosamine or galactosamine was observed from the amino acid composition analysis. This leads to the conclusion that the 8th residue is composed of Cys.

As a second amino acid sequence analysis technique, applicants fractionated the molecule at the argine residues with the enzyme trypsin. To prevent the trypsin from also cleaving the IL-1 molecule at the lysine sites, the side chains of the lysine molecule were protected with a specific blocking agent. Preferably, the trypsin is treated with L-1-tosylamino-S-phenylethylchloromethylketone ("TPCK") to deactivate other contaminating enzymes, such as chymotryspin, that may also be present, thereby minimizing the possibility that the IL-1 protein will be cleaved at other residues. It is to be understood that rather than employing trypsin, other enzymes may be used to cleave the IL-1 molecules at other residue sites.

After cleavage of the IL-1 molecule, the resulting peptides were separated on the basis of hydrophobocity by HPLC procedures. The HPLC technique used in the present invention preferably employs a reversed phase, octadecyl bonded silica column having a pore size sufficiently large to be optimally utilized with the proteinaceous IL-1 peptides, i.e., a pore size of at least 300 Å.

Suitable reversed phase HPLC columns for use in the practice of the present invention are articles of commerce. A preferred column for this purpose is the Vydac 218 TP reversed phase column commercially available from Separations Group, Hesperia, Calif. This column consists of octadecyl silane groups covalently bonded by means of a siloxane (silican-oxygen-silicaon) bond to the surface of the 300 Å pore diameter silica gel which has been classified to a mean particle size of 5 microns. It is to be understood that the use of other reversed phase columns is within the scope of the present invention.

The IL-1 peptides that are bonded to the octadecyl column are eluted by the use of a linear gradient of acetonitrile. A preferred gradient for this purpose is a 0 to 95% (v/v) acetonitrile gradient in trifluoroacetic acid (TFA), pH 2.0.

The eluted peptides can be conveniently monitored with commercially available detection systems. For example, the relative protein concentration in the fractions eluted from the HPLC columns can be determined by measuring absorbance of the eluted material with an automated ultraviolet light spectrophotometer, at 230 nanometers wavelength. A suitable automated ultraviolet light absorbance detection apparatus is available from Waters Associates, Millford, Me. Alternatively, protein elution can be monitored with an automated fluorescence detection system, as described by Stein and Moschera, 78 *Meth. Enzymol.* 435 (1981).

The eluted HPLC fractions are analyzed in sequence by gel electrophoresis, discussed above, to determine the number of peptides contained in each of the HPLC fractions. Thereafter, the peptides are concentrated in vacuo and then analyzed for amino acid sequence. This is preferably carried out with an automated sequencing apparatus, which are articles of commerce. Through this technique, applicants have discovered that a major portion of the Il-1 molecule near the N-terminal portion of the human IL-1 molecule is composed of the following sequence of amino acid residues:
-Ser-Leu-Val-Met-Ser-Gly-Pro-Tyr-Glu-Leu-Lys-Ala-Leu-His-Leu-Gln-Gly-Gln-Asp-Met-Glu-Gln-Gln-Val-Val-Phe.

The first four residues of the amino terminal portion of this amino acid fragment corresponds with the last four residues of the C-terminal portion of the sequence determined above by automated Edman degradation technique, thus leading to the conclusion that the first 42 residues of the N-terminal portion of the Il-1 molecule is composed of the following sequence:

$NH_2$-Ala-Pro-Val-Arg-Ser-Leu-Asn-Cys-Thr-Leu-Arg-Asp-Ser-Gln-Gln-Lys-Ser-Leu- Val-Met-Ser-Gly-Pro-Tyr-Glu-Leu-Lys-Ala-Leu-His-Leu-Gln-Gly-Gln-Asp-Met-Glu-Gln-Gln-Val-Val-Phe

The products of the present invention are further illustrated by the following examples.

EXAMPLE 1

IL-1 Production

Leukocyte concentrates of a volume of 350–400 ml, obtained from human whole blood (mixture from Portland, Oregon Red Cross), are mixed with and diluted in $Ca^{++}$, $Mg^{++}$ free phosphate buffered saline ("PBS") layered onto Histopaque (Sigma Chemical Company, St. Louis, Mo.) and then centrifuged at 600×g for 30 minutes at room temperature. The interface layer, consisting of the leukocytes, is recovered, washed with PBS and centrifuged at 400×g for 10 minutes at room temperature. The cells are washed two more times in $Ca^{++}$, $Mg^{++}$ free PBS and centrifuged at 200×g for 10 minutes after each washing.

The resulting mononuclear cells in a concentration of $2\times10^6$ cells/ml are cultured in spinner flasks in MEM Medium. The medium is supplemented with 50 U/ml penicillin, 50 ug/ml streptomycin, 2 mM glutamine, 0.2 mM gentamycin, 10 mM HEPES, pH 7.4. The cells are stimulated into IL-1 production by the addition of 0.01 mg/ml of heat inactivated, formalin fixed, *Staphylococcus aureus* (Igsorb, The Enzyme Center, Inc., Malden, Mass.). To reduce the production of contaminating proteins, serum is not added to the culture medium. Following incubation for 24 hours at 35° C. in a humidified atmosphere of 5% $CO_2$ in air, the culture is centrifuged at 7000×g for 30 minutes at room temperature and then the supernatant removed and stored in polypropylene bottles at −20° C. until used.

EXAMPLE 2

Ion Exchange Chromatography

IL-1 containing supernatants as prepared in Example 1, are purified by cation exchange chromatography and anion exchange chromatography. These chromatography procedures were performed at 4° C. and the gels used therein are pretreated with 0.1% Triton-X and 10% v/v fetal calf serum to reduce non specific absorption of IL-1 activity to the resins. Prior to the chromatography procedures, the culture supernatant is assayed, as described above. The crude IL-1 solutions have been found to have a typical total activity of $1.98\times10^7$ U, a specific activity of $6.37\times10^4$ U/rag of sample and a total protein content of $3.11\times10^5$ ug.

A. Cation Exchange Chromatography

The ionic strength of the culture supernatant is adjusted by addition of 1M sodium citrite buffer, pH 4.0, to a final concentration of 10 mM citrite and also was reduced to a pH of 4.0 with concentrated HCl. The supernatant as thus adjusted is applied to 30×1.6 cm column of sulfopropyl Sephadex ("SPS") C-25 (Pharmacia Fine Chemicals, Piscataway, N.J.) which has been previously equilibrated with the same buffer together with 150 mM NaCl, pH 4.0. The culture supernatant is applied to the column at a rate of 400 ml/hour.

After loading has been completed, the column is washed with 10 column volumes of 10 mM 2-N-morpholino ethanesulfonic acid ("MES") buffer, pH 5.0, to remove unbound protein. The bound protein is then eluted from the column with four column volumes of 10 mM Tris-HCl, pH 8.1, applied to the column at a rate of 50 ml/hour. The pH of a column has been found to rise after application of approximately three column volumes of the eluant thereby resulting in elution of the IL-1 peak. Column fractions are collected and assayed as discussed above.

Applicants have found that the IL-1 eluted from the cation exchange column has exhibited an activity of approximately $1.1\times10^7$ U and specific activity of approximately $2.10\times10^5$ U/mg thereby achieving approximately a 140 fold increase in IL-1 activity while retaining approxmately 56% of the initial IL-1. Also, approximately 80% of the contaminating proteins are removed by the cationic exchange chromatography procedure.

B. Anion Exchange Chromatography

The pooled concentrate from the cation exchange column is further purified by anion exchange chromatography on a column of DEAE-Sephacel (Pharmacia Fine Chemicals, Piscataway, N.J.). The DEAE-Sephacel column is equilibrated with 10 mM Tris-HCl, pH 8.1. Since the IL-1 is eluted off the SPS column with this same equilibration buffer, the SPS pool is loaded directly onto the DEAE-Sephacel column at a rate of 20 ml/hr, thereby avoiding any loss of activity by dialysis. After loading, the column is washed with five column volumes of the same equilibrating buffer and then elution is carried out with a linear gradient of four column volumes of 0–400 mM NaCl in 10 mM Tris-HCl, pH 8.1.

Applicants have found that the IL-1 activity eluted in a sharp peak at 0.08–0.12M NaCl. SDS-PAGE analysis of the elution fractions revealed some high molecular weight contaminants as well as three major bands of molecular weights of approximately 17,500, 15,000 and 12,000 daltons. Analysis of the column eluate revealed a total activity of $7.75\times10^6$ U, a specific activity of $2.58\times10^6$ U/mg, total protein of $3\times10^3$ ug and a yield of approximately 39%.

EXAMPLE 3

Affinity Chromatography

The active fractions from Example 2 are pooled for further purification by affinity chromatography technique employing a 10×1.6 cm column of the dye-ligand "Procion" red dye coupled to an agarose matrix (Bethesda Research Laboratories, Bethesda, Md., Cat. No. 5926 SA) that has been preequilibrated in 10 mM Tris-HCl buffer, pH 8.1. To optimize the binding of the IL-1 to the dye-ligand column, the ionic strength of the DEAE-Sephacel pool is lowered to below 40 mM by dilution of the pool 1:4 in 10 mM Tris-HCl buffer, pH 8.1. The dye-ligand column is initially washed with four column volumes of the same starting buffer to remove unbound protein and then elution is carried out with a linear gradient composed of fifteen column volumes of 0 to 1.0M NaCl in 10 mM Tris-HCl buffer, pH 8.1. Applicants have found that the IL-1 activity typically is eluted in a sharp peak at 0.50–0.55M NaCl. Column fractions are collected and assayed as described above.

SDS-PAGE analysis of the IL-1 active fractions has revealed a single protein band having a molecular weight of approximately 17,500 daltons. The high molecular weight bands, noted above, are eluted in the flow through from column and the lower molecular weight bands of 15,000 and 12,000 daltons are eluted at a higher salt concentration. Assays conducted on the active IL-1 fractions have shown a total activity of the IL-1 of about $6.2\times10^6$ U, a specific activity of about $9.5\times10^8$ U/mg, and a total protein content of approximately 6.5 ug. This equates to an overall purity of IL-1 of greater than 99% and a yield of approximately 31% from the starting supernatants. It is clear from the single protein band which resulted from the SDS-PAGE and silver staining of the fractions collected after dye-ligand affinity chromatography, and also from the specific activities of the fractions analyzed, that essential homogeneity of the IL-1 molecule was achieved by the present invention while maintaining a high yield of the IL-1.

The homogeneous IL-1 obtained from the dye-ligand affinity chromatography is also analyzed by two-dimensional polyacrylamide gel electrophoresis together with silver staining, as noted above. This procedure consistently has yielded four staining spots at exactly the same molecular weight, i.e., 17,500 daltons and stained the same color in silver stain. The spots are always in the same position and the same relative proportions regardless of which lot of starting supernatant is used. The most intense spot has indicated a pI of 6.3–5.9. The other three spots stain less intensely as the pH gradient becomes more acid. These results indicate that human IL-1 exists in vivo in different charged states, perhaps caused by different states of amidation. The fact that the silver staining yields the exact same color for each spot indicates that the same parent protein most likely is staining in all cases.

EXAMPLE 4

Affinity Chromatography-Blue Dye

The active fractions from Example 2 are pooled and then further purified by the affinity chromatography technique set forth above in Example 3 with the exception that the dye ligand is composed of Cibacron® Blue 36A dye cross-linked to an agarose matrix (Bethesda Research Laboratories, Bethesda, Md., Cat. No. 5904 SA). Assays conducted on the active fractions have shown a total activity of the IL-1 of about $5.0 \times 10^6$ U and a specific activity of about $7.6 \times 10^8$ U/mg, which is approximately 80% of the activity present in the red dye derived IL-1. To achieve greater purity, the affinity chromatography process can be repeated with the active fractions from the first procedure.

EXAMPLE 5

Amino Acid Composition Analysis

Purified IL-1 from Examples 3 or 4 is boiled in vacuo in 5.7N HCl (redistilled from concentrated HCl (Kodak, Rochester, N.Y.)) for twenty-four and forty-eight hours to cause hydrolysis of peptide bonds and release of free amino acids. After hydrolysis, samples are dried under vacuum and then resuspended in 0.2N sodium citrate, pH 2.2. The samples are then injected into a single column LKB Model 4150-Alpha (Cambridge, England) amino acid analyzer which employs ninhydrin detection. The areas of the output "peaks" corresponding to the quantities of particular amino acids present are integrated with an LKB Model 2220 recording integrator.

The amino acid composition of human IL-1 as determined by the present technique is set forth in Table I below. As indicated by Table I, no glucosamine or galactosamine has been observed from the above amino acid analysis which corresponds with applicants' prior findings that human IL-1 migrates as a single molecular weight species on polyacrylamide gels. One or both of these observations would likely be contrary if human IL-1 includes attached carbohydrate moieties. Thus, it is unlikely that human IL-1 is a glycoprotein.

TABLE I

| Amino acid analysis of human IL-1 | |
|---|---|
| Amino Acid | No. of Residues per Molecule |
| Asp/Asn | 14 |
| Thr | 8 |
| Ser | 11 |
| Glu/Gln | 22 |
| Pro | 6 |
| Gly | 11 |
| Ala | 8 |
| Cys | 1* |
| Val | 11 |
| Met | 4 |
| Ile | 6 |
| Leu | 11 |
| Tyr | 4 |
| Phe | 11 |
| His | 3 |
| Lys | 13 |
| Arg | 3 |

*Determined from amino acid sequence analysis.

EXAMPLE 6

Amino Acid Sequence Analysis

Fractions containing homogeneious IL-1 from the dye-ligand affinity chromatography procedures of Examples 3 or 4 initially are diluted 10-fold with deionized distilled water, adjusted to pH 4.0 with 1N HCL and applied to a 0.5 ml bed volume SPS C-25 chromatography column. Prior to the application of the IL-1, the column is equilibrated with a buffer composed of 0.1M sodium citrate, 0.05M NaCl, pH 4.0. After loading of the IL-1, the column is washed with 10 ml of the same equilibration buffer followed with 20 ml of deionized, distilled water. Thereafter, the IL-1 is eluted with 10 mM sodium borate, pH 9.0.

In a first sequencing analysis procedure, 11.1 ug of homogeneous IL-1, as concentrated above, is dried under vacuum and then subjected directly to automated amino terminal Edman degradation using an Applied Biosystems Model 470 protein sequencer. By this process applicants have discovered that the N-terminal portion of the IL-1 molecule is composed of the following sequence of amino acid residues:

Ala-Pro-Val-Arg-Ser-Leu-Asn-Cys-Thr-Leu-Arg-Asp-Ser-Gln-Gln-Lys-Ser-Leu-Val-Met

In a second sequencing analysis procedure the homogeneous Il-1 is fractionated with the enzyme trypsin and then subjected to automated sequencing analysis. Prior to fractionation of the IL-1 molecules with trypsin, the side chains of the lysine residues are blocked with the specific agent citraconic anhydride. To this end, fractions from the SPS C-25 column eluate are concentrated in vacuo to a final volumn of 1 ml. One ul of citraconic anhydride (Pierce) is added to the concentrated IL-1 and then the pH adjusted to 8.3 with 5N NaOH. The reaction mixture is stirred for 15 minutes and allowed to stand at room temperature for 1 hour. At that time, a second 1 ul quantity of citraconic anhydride is added, the reaction mixture is stirred for an additional 15 minutes and then the mixture is adjusted to final pH of 8.3 with 5N NaOH. After standing at room temperature for an additional hour, 100ul of 1M Tris-HCl, pH 7.4 and 100ul of 1M NH₄HCO₃, pH 7.8 are added to the reaction mixture to complete the blocking process.

Next, 2 ug of TPCK-treated trypsin (Worthington) (in 10 ul of 10 mM HCl, pH 2.0) is added to the reaction mixture to cleave the IL-1 molecule at the arginine residues. After addition of the trypsin, the mixture is gently stirred for 5 seconds and then incubated at 37° C. for two hours. After completion of the incubation period, an additional 2 ug of TPCK-treated trypsin is added and the mixture incubated at 37° C. for an additional 2 hours. The mixture is then cooled to room temperature and adjusted to pH 2.5 with 90% formic acid (Baker). After standing for 4 hours at room temperature, the acidified mixture is diluted by adding 0.5 ml of 6M guanidine-HCl and then injected onto a 4.6× 250 mm Vydac 218 TP column, which has been previously equilibrated with 0.1% TFA (v/v) in water, at a flow rate of about 1 ml/min. with a Beckman Model 112 pump (Beckman Instruments, Division of Smith Kline Beckman). The loaded column is initially washed with 0.1% TFA (v/v) in water to remove non-bound components and then the IL-1 peptides are eluted from the column with a linear gradient of 0–100% acetonitrile in 0.1% TFA (v/v) at a rate of 0.5%/min. at a flow rate of 1 ml/min. The elution of the peptides is detected by ultraviolet light spectrophotometry at 230 nanometers wavelength.

Individual fractions or pools composed of two or more fractions containing IL-1 peptides are sequenced by automated amino terminal Edman degradation. Prior to the sequencing, the HPLC fractions containing IL-1 are analyzed by gel electrophoresis to determine the number of peptides in each fraction. Thereafter, the peptides are concentrated in vacuo to final volumes of approximately 30 ul, spotted onto a conditioned filter and then dried in a heating chamber at 44° C. The dried filter is placed into an Applied Biosystems Model No. 470A automated protein sequencer. By this procedure, applicants have discovered that a major fragment of the human IL-1 molecule near the N-terminal portion thereof is composed of the following sequence of amino acid residues: Ser-Leu-Val-Met-Ser-Gly-Pro-Tyr-Glu-Leu-Lys-Ala-Leu-His-Leu-Gln-Gly-Gln-Asp-Met-Glu-Gln-Gln-Val-Val-Phe. The first four residues of the N-terminal end of this sequence coincides with the last four residues of the C-terminal end of the sequence determined above by direct automated protein sequencing, leading to the conclusion that this intermediate sequence is a continuation of the N-terminal sequence set forth above.

As will be apparent to those skilled in the art to which the invention is addressed, the present invention may be carried out by using IL-1 sources, culture media, culture media additives, culture conditions, purification techniques and sequences of use, chromatography columns, assays and other materials and techniques in addition to those specifically discussed above without departing from the spirit or essential characteristics of the invention. The particular materials and processes described above are therefore to be considered in all respects as illustrative and not restrictive. The scope of the present invention is as set forth in the appended claims rather than being limited to the examples of the materials and processes set forth in the foregoing description.

The embodiments of the invention in which an exclusive property or privilege is claimed are defined as follows:

1. A process for purifying a mature interleukin-1B from a crude solution of interleukin-1 free of serum proteins, comprising the steps of:
   (A) exposing the crude solution of interleukin-1 to a red triazinyl dye-ligand bound to a support matrix;
   (B) washing unbound components of the crude solution from the support matrix; and
   (C) eluting a mature interleukin-1B from the dye-ligand.

2. The process of claim 1, wherein said interleukin-1B is eluted from the dye-ligand with a salt gradient.

3. The process of claim 2, wherein the ionic strength of crude solution of interleukin 1 is lowered to below 40 mM prior to exposure to the triazinyl dye-ligand.

4. The process of claim 3, wherein the gradient is in the range of from 0.5 to 0.55 molar NaCl.

5. The process of claim 1, further comprising, prior to step (A), a step (D) of subjecting the crude solution of interleukin-1 to ion exchange chromatography.

6. The process of claim 1, wherein the triazinyl dye-ligand is bound to high molecular weight dextran which in turn is bound to the support matrix.

7. The process of claim 5, wherein step (D) comprises (i) passing the crude solution over a first matrix having either a positively- or negatively-charged first group, (ii) eluting bound interleukin-1 from the first matrix; (iii) pooling fractions that exhibit interleukin-1 activity; (iv) passing pooled fractions obtained in step (iii) over a second matrix having a group charged oppositely to the first group; (v) eluting bound interleukin-1 from the second matrix; and (vi) pooling fractions that exhibit interleukin-1 activity.

8. A purified, mature human IL-1β polypeptide having:
   (i) a molecular weight of 17,500 daltons as determined by SDS-PAGE,
   (ii) an N-terminus of Ala-Pro-Val-Arg-Ser-Leu-Asn-Cys-Thr, where alanine is the N-terminal amino acid, and
   (iii) IL-1 biological activity in a thymocyte proliferation assay of at least $7.6 \times 10^8$ U/mg.

9. A polypeptide according to claim 8, having a specific activity in said thymocyte proliferation assay of about $9.8 \times 10^8$ U/mg.

10. A polypeptide according to claim 8, wherein said N-terminus comprises Ala-Pro-Val-Arg-Ser-Leu-Asn-Cys-Thr-Leu-Arg-Asp-Ser-Gln-Gln-Lys-Ser-Leu-Val-Met.

11. A polypeptide according to claim 8, wherein said N-terminus comprises Ala-Pro-Val-Arg-Ser-Leu-Asn-Cys-Thr-Leu-Arg-Asp-Ser-Gln-Gln-Lys-Ser-Leu-Val-Met-Ser-Gly-Pro-Tyr-Glu-Leu-Lys-Ala-Leu-His-Leu-Gln-Gly-Gln-Asp-Met-Glu-Gln-Gln-Val-Val-Phe.

12. A polypeptide according to claim 8, wherein said polypeptide is detected as a single band by SDS-PAGE and silver staining, and is sufficiently homogeneous to be amino-acid sequenced by direct Edman degradation.

\* \* \* \* \*

(12) EX PARTE REEXAMINATION CERTIFICATE (5100th)
United States Patent
Kronheim et al.

(10) Number: US 5,484,887 C1
(45) Certificate Issued: Apr. 26, 2005

(54) HOMOGENEOUS INTERLEUKIN 1

(75) Inventors: Shirley R. Kronheim, Seattle, WA (US); Carl J. March, Seattle, WA (US); Paul J. Conlon, III, Seattle, WA (US); Thomas P. Hopp, Seattle, WA (US)

(73) Assignee: Immunex Corporation, Seattle, WA (US)

Reexamination Request:
No. 90/004,176, Mar. 11, 1996

Reexamination Certificate for:
Patent No.: 5,484,887
Issued: Jan. 16, 1996
Appl. No.: 06/676,533
Filed: Nov. 30, 1984

Related U.S. Application Data (63) Continuation-in-part of application No. 06/635,006, filed on Jul. 27, 1984, now abandoned, which is a continuation-in-part of application No. 06/622,201, filed on Jun. 19, 1984, now abandoned.

(51) Int. Cl.$^7$ .......................... C07K 14/545; C07K 1/00
(52) U.S. Cl. ..................... 530/351; 424/85.2; 530/412; 530/413; 530/414; 530/417; 530/351; 435/69.52; 930/141
(58) Field of Search ................................ 530/351, 412, 530/413, 414, 417; 435/69.1, 69.52; 424/85.1, 85.2

(56) References Cited

PUBLICATIONS

C.A. Dinarello et al., PNAS 74:4624, 1977.*
K. Welte et al., J. Exp. Med. 156:454, 1982.*
Callard et al., *The Cytokine Factsbook*, Academic Press, London, 1994 at pp. 31–33 and 37–38.*
Dinarello, C.A. et al. (1977) "Human Leukocytic Pyrogen: Purification and Development of a Radioimmunoassay" Proceedings of the National Academy of Sciences USA 74(10):4624–4627.
Rosenwasser, L.J. et al. (1981) "Ability of Human Leukocytic Pyrogen to Enhance Phytohemagglutinin Induced Murine Thymocyte Proliferation" Cellular Immunology 63:134–142.
Kronheim, S.R. et al. (1985) "Human Interleukin 1: Purificaiton to Homogeneity" J. Exp. Med. 161:490–502.
Dinarello, C.A. (1980) "Endogenous Pyrogens" Fever pp. 1–9.

* cited by examiner

*Primary Examiner*—Lorraine Spector (57) ABSTRACT

Interleukin 1 has been purified by use of various techniques including ion exchange chromatography and dye-ligand affinity chromatography. By these techniques, interleukin 1 has been purified to homogeneity. The high purification of interleukin 1 has enabled the amino acid composition of this protein to be ascertained and its amino acid sequence to be partially determined.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–7 is confirmed.

Claims 8–12 are cancelled.

\* \* \* \* \*